United States Patent
Colman

Patent Number: 5,709,650
Date of Patent: Jan. 20, 1998

[54] ORTHOPEDIC DEVICE UTILIZING HYPOALLERGENIC NON-INFLAMMATORY ADHESIVE

[76] Inventor: John P. Colman, 14566 El Puente Way, Saratoga, Calif. 95070

[21] Appl. No.: 659,193

[22] Filed: Jun. 6, 1996

[51] Int. Cl.⁶ ............................................. A61F 5/00
[52] U.S. Cl. .......................... 602/52; 602/12; 602/27; 602/60; 602/62; 602/65; 128/DIG. 15
[58] Field of Search ..................... 602/12, 20, 23, 602/24, 25, 26, 27, 28, 29, 30, 41, 42, 52, 53, 54, 60, 61, 62, 63, 64, 65, 66, 74, 75, 78, 79; 128/845, 846, 869, 870, 871, 877, 878, 879, 881, 882, 887, 888, 889, DIG. 15; 24/304, 306

[56] References Cited

U.S. PATENT DOCUMENTS

| | | | |
|---|---|---|---|
| 4,941,237 | 7/1990 | Hovis | 24/304 |
| 4,977,891 | 12/1990 | Grim | 602/27 |
| 4,981,132 | 1/1991 | Chong | 602/27 X |
| 5,348,530 | 9/1994 | Grim et al. | 602/12 X |

Primary Examiner—Lynne A. Reichard
Assistant Examiner—Kim M. Lu
Attorney, Agent, or Firm—Townsend and Townsend and Crew LLP

[57] ABSTRACT

An orthopedic appliance for reinforcing a patient's skeletal anatomy from a rigid shell fitted at the inside to the patient at skin overlying the skeletal anatomy to be reinforced, has an improvement for adhering the rigid shell to the skin of the patient. A strip of flexible tensile tape has a first side for fitting to the skin of a patent and a second side outward exposed for fitting to the inside of the rigid shell. A hypoallergenic non-inflammatory adhesive is coated on one side of the strip of flexible tape for fitting to the skin. Means for removable attachment to the inside of the rigid shell is placed on the second side of the strip of flexible tape for outward exposure and attachment to the rigid shell. Complimentary means for removable attachment is fitted to the inside of the rigid shell. This attachment transfers loading from the skin of the patient to the rigid shell for orthopedically reinforcing the skeletal anatomy of the patient. The disclosed invention finds preferred use with joint reinforcing appliances such as ankle, knee, and elbow braces.

8 Claims, 2 Drawing Sheets

ORTHOPEDIC DEVICE UTILIZING HYPOALLERGENIC NON-INFLAMMATORY ADHESIVE

This invention relates to orthopedic appliances for reinforcing the limbs in body movement. More particularly, an orthopedic appliance having rigid members, such as an activity knee brace, is provided with removeably detachable hypoallergenic non-inflammatory adhesive strips to rigidly secure the appliance against the dynamics of bodily movement.

BACKGROUND OF THE INVENTION

Limb reinforcing orthopedic appliances having rigid or semi-rigid shell members are well known. A good example of such an orthopedic appliance can be the knee brace appliance. In such knee braces, there typically includes an upper portion which attaches to and moves with the thigh, a lower portion that attaches to and moves with the calf, and a hinge mechanism therebetween. The thigh portion and calf portion of the brace are composed of rigid shells. These rigid shells fit to the skin of the brace wearer and transfer from the skin to the brace dynamic loading that would otherwise be transmitted to and through the joint which the braces reinforces. For example, in the case of the knee brace, this force is transmitted from the skin to the hinge of the knee brace.

Precise positioning of the orthopedic braces from their exterior fit to the skin is required. For example, in the case of the knee brace, it is necessary that the hinge mechanism of the brace have precise coincidence to the joint of the knee of the wearer.

It is also well known that such devices are notoriously hard to maintain in precise fitted relationship on the patient. This situation is especially aggravated with the well conditioned male athlete.

Take the case of a well conditioned athlete utilizing a knee brace—such as a player of American football. In most knee braces, positioning of the thigh portion of the brace is made by having so-called "condylar pads" contact the condyle of the femur. These pads rest on the flared portion of condyle to prevent "pistoning" of the brace from the thigh out over the knee with resultant movement of the hinge of the brace out of coincidence to the joint of the knee.

Unfortunately, the well conditioned athlete typically has a cone shaped thigh with the apex of the cone adjacent the knee and the base of the cone extending to and toward the hip. Conventional knee brace keying to the condyle of the femur is generally unsatisfactory. It is common for the brace to slip downward over the joint of the knee. When such slippage occurs, the thigh portion of the brace has to be refitted before activity on the part of the athlete can resume.

SUMMARY OF THE INVENTION

An orthopedic appliance for reinforcing a patient's skeletal anatomy from a rigid shell fitted at the inside to the patient at skin overlying the skeletal anatomy to be reinforced, has an improvement for adhering the rigid shell to the skin of the patient. A strip of flexible tensile tape has a first side for fitting to the skin of a patent and a second side outward exposed for fitting to the inside of the rigid shell. A hypoallergenic non-inflammatory adhesive is coated on one side of the strip of flexible tape for fitting to the skin. Means for removable attachment to the inside of the rigid shell is placed on the second side of the strip of flexible tape for outward exposure and attachment to the rigid shell. Complimentary means for removable attachment is fitted to the inside of the rigid shell. This attachment transfers loading from the skin of the patient to the rigid shell for orthopedically reinforcing the skeletal anatomy of the patient. The disclosed invention finds preferred use with joint reinforcing appliances such as ankle, knee, and elbow braces.

DESCRIPTION OF THE PREFERRED EMBODIMENT

Figure 1:
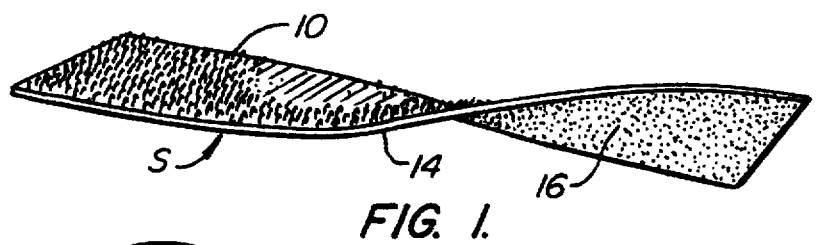
FIG. 1 is a view of a typical flexible strip for reinforcing the fit of a skeletal reinforcing shell to the skin of a patient wearing an orthopedic appliance illustrating hypoallergenic non-inflammatory adhesive on one side of the brace and Velcro® (a product of Velcro® U.S.A., Inc. of Manchester, N.H.) tape affixed to the opposite side of the tape for holding the shell of an orthopedic brace to the skin of a patient.

Referring to FIG. 1, adhesive strip S utilized with this invention is illustrated. Adhesive strip S includes tensile fabric 14 which imparts an inelastic resistance to tension throughout the strip; it is not desirable that adhesive strip S include any appreciable degree of elasticity. On the skin confronting side, adhesive strip S includes a coating of hypoallergenic non-inflammatory adhesive 16. On the opposite side facing away from the skin, a mechanism (10) for fastening to the inside shell of a brace is included. I prefer Velcro® tape, a registered trade mark of Velcro U.S.A., Inc. of Manchester, N.H. Since it is well known that this tape requires a hook and pile combination, I prefer to place hook tape to adhesive strip S and pile tape to the shell of any brace.

Figure 2A:
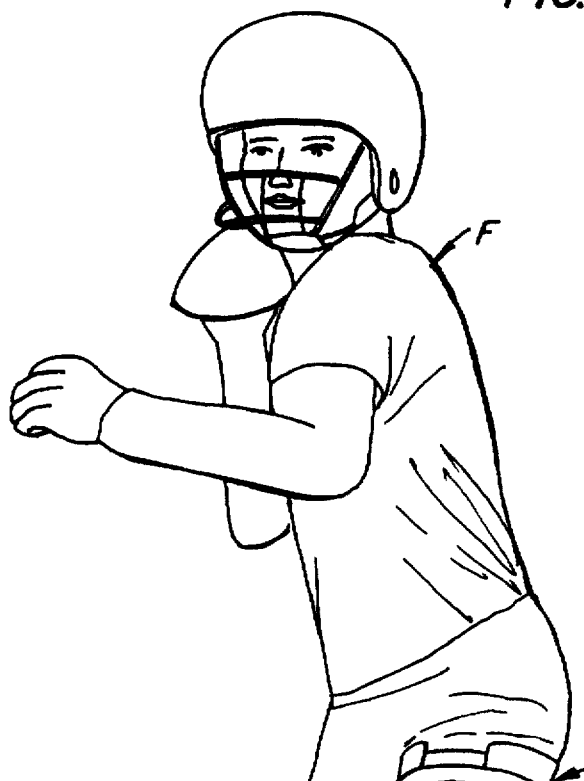
FIG. 2A is a view of a player of American football wearing a conventional activity knee brace, this conventional activity knee brace being held in place by adhesive in accordance with this invention.

Referring to FIG. 2A, football player F is illustrated having left leg L in activity brace B. Simply stated thigh shell 20 fastens to the thigh of left leg L, calf shell 22 fastens to the calf of left leg L, and hinge member H couples the two shell members together. Hinge member H acting to calf shell 22 and thigh shell 20 serves to relieve the knee of left leg L from dynamic loading of activity that could otherwise strain the knee.

Figure 2B:
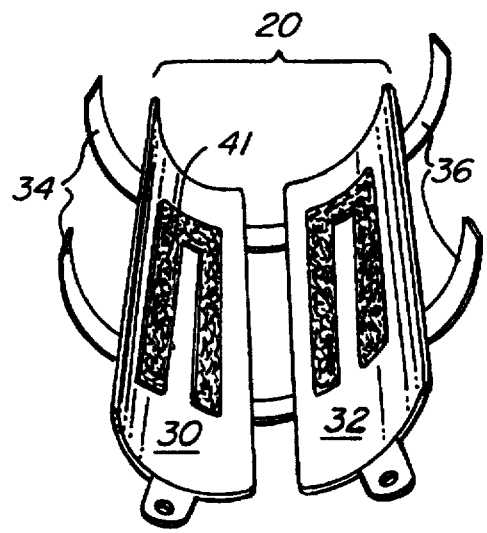
FIG. 2B is a view of the interior of one of the shells of the activity brace shown in FIG. 2A illustrating the placement of Velcro® tape for holding the adhesive of this invention in place.

Referring to FIG. 2B, thigh shell 20 is illustrated as a two part member having first shell half 30 and second shell half 32. As is conventional, tape members 34 and 36 effect fastening of first shell half 30 and second shell half 32 about left leg L at the thigh to fasten the upper member of the brace to the leg of football player F.

The reader will understand that braces for the knee come in many differing varieties. This being the case, further illustration will not be added except to state that the invention herein does require a brace having a shell member construction. Typically, such shell members are at least semi-rigid if not totally rigid. They have sufficient strength when fastened to the skin of football player F to transfer to thigh shell 20 through the skin of the wearer forces that would other load the skeletal frame and knee.

Figure 2C:
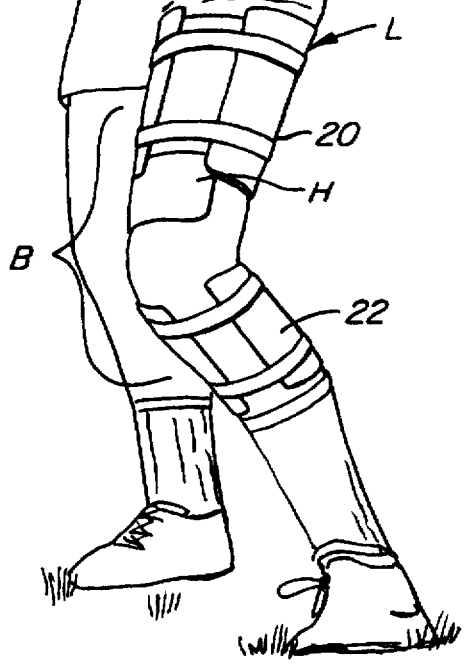
FIG. 2C is a perspective view of the adhesive strip, the strip being illustrated having the hypoallergenic adhesive on one side and the Velcro® tape attaching material on the opposite side.
Figure 2C:
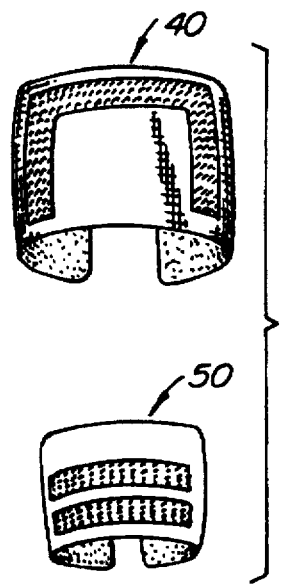

Referring to FIG. 2C, thigh pad 40 and calf pad 50 are illustrated. These pads are applied before the respective sections of the shells of activity brace B are placed on left leg L of football player F. In construction, thigh pad 40 and calf pad 50 are shown having strips of Velcro® located at various locations on the respective shell exposed backings of the pads. These respective backings match with mating Velcro® backing 41 fastened to first shell half 30 and second shell half 32 of thigh shell 20 (as shown in FIG 2B). It is in this releasable mating that adhesive strips S of this invention has it advantage.

This advantage can be simply stated. In the case of knee activity brace B, left leg L of football player F from the thigh toward the knee has a cone shape. This cone shape has its base toward the hip of football player F and the apex toward the knee. In the prior art, all manner of devices have been used to keep knee activity brace B from slipping down and over the knee. Specifically, and most usually, pads fitting to the condyle of the femur have been used. The reader will understand from experience that muscular legs present little profile of the condyle of the femur for preventing downward slippage. Further, and once downward slippage occurs, hinge member H is no longer co-incident to the joint of the knee. Activity must stop and the brace must be readjusted.

With the adhesive strips of this invention, firm adhesion to the skin over a large area favorably transfers loading to the shells of the brace.

Figure 3A:
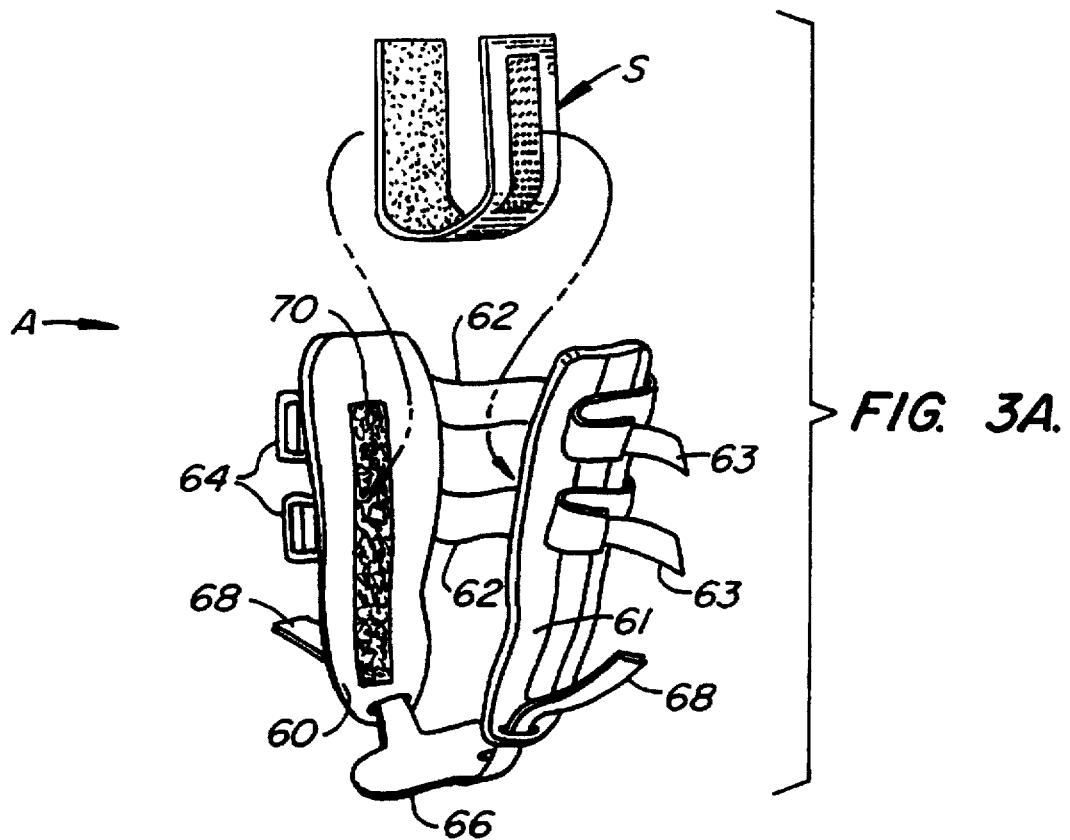
FIG. 3A is an exploded view with this invention in combination with an ankle brace with the adhesive pad shown overlying the brace ready to receive an ankle to be protected and the brace underlying the adhesive pad; and, FIG. 3B illustrates a foot placed within the ankle brace with the brace shown in the process of initial fastening.
Figure 3B:
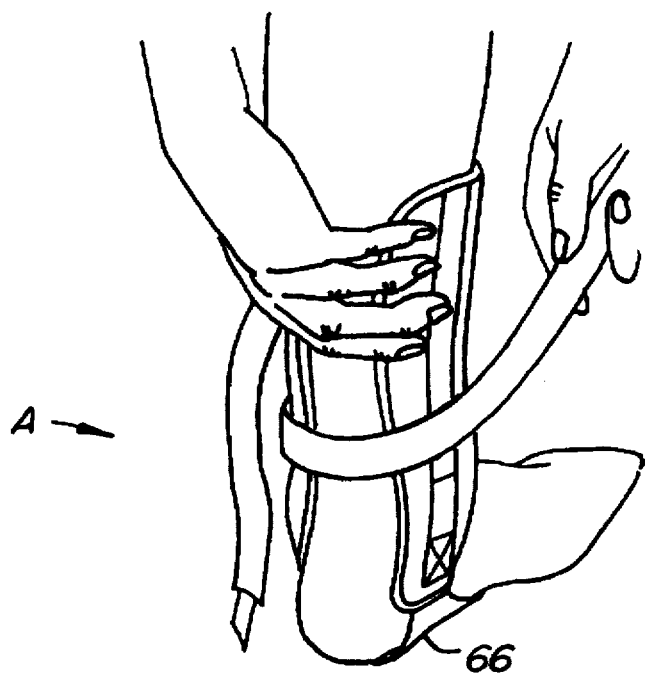

Referring to FIG. 3A and 3B, the use of this invention with ankle brace A is illustrated. Specifically, it is common to tape ankles with regular adhesive tape. Unfortunately, this is a time consuming enterprise. Further, the tape utilized is expensive. A substitute for this practice is shown in FIGS. 3A and 3B.

Referring to FIG. 3A, ankle brace A is illustrated having first ankle shell 60 and second ankle shell 61. The respective first ankle shell 60 and second ankle shell 61 are hinged at hinge strips 62 and fastened over the ankle of a patient by fastening straps 63 and buckles 64. As is conventional in this type of brace, heel strap 66 with tightening straps 68 fastens ankle brace A over the foot.

It is required that Velcro® strip 70 as shown in first ankle shell 60 be placed interior of both first ankle shell 60 and second ankle shell 61.

Overlying ankle brace A is shown adhesive strip S which can be placed under the heel of a patient and up along both sides of left leg L at the ankle. In use, this strip is first placed with the adhesive side addressed to the skin and the Velcro® side exposed to the respective shell members. Once this adhesive strip S is in place, first ankle shell 60 and second ankle shell 61 are secured into place as illustrated in FIGS. 3B.

It will be understood that I have shown just two simple examples of the use of my invention. In the case of FIGS. 2A, 2B and 2C, I have shown a brace having two separate shell members joined by hinge member H. In the case of FIGS. 3A and 3B, I have shown a single shell member placed over a joint—in this case the ankle. Understanding this much, the reader can readily determine that this invention can be utilized in many different orthopedic appliances without limitation.

What is claimed is:

1. In an orthopedic appliance for reinforcing a patient's skeletal anatomy, the appliance comprising at least a pair of rigid shells, each rigid shell having an inside and an outside, the inside of each rigid shell adapted to receive a patient's skin overlying the skeletal anatomy to be reinforced, the improvement for adhering the rigid shells to the skin of the patient comprising:

a strip of flexible tape having a first side for fitting to the skin of a patient and a second side outward exposed for fitting to the inside of the rigid shells;

a hypoallergenic non-inflammatory adhesive coated on one side of the strip of flexible tape for fitting to the skin;

means for removable attachment to the inside of the rigid shells on the second side of the strip of flexible tape for outward exposure to the rigid shells; and, complimentary means for removable attachment fitted to the inside of the rigid shells for attachment of the rigid shells to the strip of flexible tape to transfer loading from the skin of the patient to the rigid shells for orthopedically reinforcing the skeletal anatomy of the patient.

2. In an orthopedic appliance for reinforcing a patient's skeletal anatomy according to claim 1 and wherein:

the orthopedic appliance includes first and second rigid shell member connected by a hinge.

3. In an orthopedic appliance for reinforcing a patient's skeletal anatomy according to claim 1 and wherein:

the orthopedic appliance includes first and second rigid shell members for fitting over one another with a limb of a patient therebetween.

4. In an orthopedic appliance for reinforcing a patient's skeletal anatomy according to claim 1 and wherein:

a plurality of strips of flexible tape are utilized to fasten each shell to the skin of the patient.

5. A method of fastening an orthopedic appliance to a patient's skin for reinforcing the patient's skeletal anatomy, comprising the steps of pair of rigid shells for fitting to the skin of a patient overlying skeletal anatomy of the patient to be reinforced;

providing a strip of flexible tape having a first side for fitting to the skin of a patient and a second side outward exposed for fitting to the inside of the rigid shells;

applying a hypoallergenic non-inflammatory adhesive coated on one side of the strip of flexible tape for fitting to the skin;

applying means for removable attachment to the inside of the rigid shells on the second side of the strip of flexible tape for outward exposure to the rigid shells;

providing complimentary means for removable attachment fitted to the inside of the rigid shells for attachment of the rigid shells to the strip of flexible tape to transfer loading from the skin of the patient to the rigid shells for orthopedically reinforcing the skeletal anatomy of the patient;

placing the strip to the skin of a patient overlying the skeletal anatomy to be reinforced; and, placing the rigid shells of the orthopedic appliance over the strip to fasten the rigid shell of the strip to the limb of the patient.

6. A method of fastening an orthopedic appliance for reinforcing a patient's skeletal anatomy according to claim 5 and wherein:

the provided orthopedic appliances has two shells with one shell on one side of a limb of the patient and one shell on the other side of the same limb of the patient.

7. A method of fastening an orthopedic appliance for reinforcing a patient's skeletal anatomy according to claim 5 and wherein:

the provided orthopedic appliances has two shells with the two shells being joined by a hinge.

8. A method of fastening an orthopedic appliance for reinforcing a patient's skeletal anatomy according to claim 5 and wherein:

the provided orthopedic appliances has at least one shell extending across a joint of a limb.

* * * * *